United States Patent [19]

Bobra

[11] Patent Number: 5,776,054
[45] Date of Patent: Jul. 7, 1998

[54] APPARATUS FOR RETRACTING TISSUE

[76] Inventor: Dilip Bobra, 2072 E. Lavieve La., Tempe, Ariz. 85284

[21] Appl. No.: 694,481

[22] Filed: Aug. 7, 1996

[51] Int. Cl.$^6$ ............................................. A61B 11/02
[52] U.S. Cl. .................... 600/219; 600/224; 600/222; 600/328; 600/210; 600/215
[58] Field of Search .............................. 600/201, 210, 600/213, 214, 215, 216, 217, 218, 219, 222, 224, 232

[56] References Cited

U.S. PATENT DOCUMENTS

| 380,745 | 4/1888 | Chamberlin | 600/224 |
| 3,750,652 | 8/1973 | Sherwin | 600/219 X |
| 4,156,424 | 5/1979 | Burgin | 600/213 |
| 4,991,566 | 2/1991 | Shulman et al. | 600/224 X |
| 5,052,373 | 10/1991 | Michelson | 600/217 |

FOREIGN PATENT DOCUMENTS

| 1005345 | 4/1952 | France | 600/219 |

*Primary Examiner*—Beverly M. Flanagan
*Attorney, Agent, or Firm*—Parsons & Goltry; Michael W. Goltry; Robert A. Parsons

[57] ABSTRACT

A retractor for placement proximate an incision for holding back the edges of the incision, the retractor comprising a pair of substantially elongate retractor portions having outer substantially irregular edges formed along substantially the entire length thereof for engaging and holding back the opposing edges of an incision, and an expansion assembly coupled to the retractor portions for moving the retractor portions between a collapsed position and an expanded position.

9 Claims, 2 Drawing Sheets

APPARATUS FOR RETRACTING TISSUE

BACKGROUND OF THE INVENTION

1. Field of the Invention

This invention relates to medical devices.

More particularly, this invention relates to medical devices used during surgical procedures.

In a further and more specific aspect, the instant invention relates to a retractor for use in combination with surgical procedures for holding back the edges of an incision.

2. Prior Art

Surgery is normally defined as that branch of medicine concerned with diseases and conditions requiring or amenable to operative or manual procedures. When performing a surgical procedure to repair or remedy a disease or damaged portion of the body, it is normally necessary to conduct the surgery through an incision formed through outlying tissues of the body in order to gain access to internal portions of the body requiring surgical treatment. Accordingly, it is sometimes necessary to retract or hold back the edges of an incision, organs, or other tissues, in order to facilitate access to an affected region requiring surgical treatment. This task is normally carried out with a retractor.

Retractors are provided in many shapes and sizes. Typical retractors are scalp retractors, thyroid retractors, perineal retractors, mastoid retractors, and other varieties. Known retractors typically incorporate hinged arms having one or more prongs or blades formed proximate outer ends thereof. The blades or prongs engage tissues which can then be spread apart by urging the arms outwardly thereby spreading apart the tissues. Although exemplary, the blades or prongs of these prior art retractors are located only at the outer ends of the arms. As a result, only a small portion of tissue can be retracted at any one given time. Furthermore, the retraction of the edges of a long or extensive incision normally requires the use of a plurality of retractors. Additionally, the prongs and the blades of known retractors can, and normally do, occasion damage to bodily tissues which is undesirable.

It would be highly advantageous, therefore, to remedy the foregoing and other deficiencies inherent in the prior art.

Accordingly, it is an object of the present invention to provide a new and improved retractor.

Another object of the present invention is to provide a retractor that is easy to use.

And another object of the present invention is to provide a retractor that is inexpensive to manufacture.

Still another object of the present invention is to provide a retractor for providing a greater degree of tissue retraction.

Yet another object of the instant invention is to provide a retractor that will not occasion damage to bodily tissues.

SUMMARY OF THE INVENTION

Briefly, to achieve the desired objects of the instant invention in accordance with a preferred embodiment thereof, provided is a retractor for holding back the edges of an incision. The retractor is comprised of a first retractor portion and a second retractor portion. In a first embodiment the first retractor portion includes a first retractor arm having an inner end, an inner edge and a substantially irregular outer edge. The second retractor portion includes a second retractor arm disposed parallel to and spaced from the first retractor arm, and includes an inner end, an inner edge and a substantially irregular outer edge. The first retractor arm and the second retractor arm are coupled in pivotal relation proximate the inner ends thereof for pivotal movement between a contracted position and an expanded position. An expansion assembly, coupled to the first retractor arm and the second retractor arm, is operative for facilitating the movement of the first retractor arm and the second retractor arm between the contracted position and the expanded position. The retractor is sized for receipt within an incision, with the substantially irregular outer edges of the first retractor arm and the second retractor arm being operative for engaging substantially the entire length of the edges of the incision thereby facilitating a high degree of tissue retraction when the first and second retractor arms are moved into the expanded position. In an alternate embodiment, the first and second retractor arms may be removably coupled to the expansion assembly.

In an alternate embodiment, the first and second retractor portions may include a first pair of retractor arms and a second pair of retractor arms coupled together in spaced apart and substantially parallel and pivotal relation. The first pair of retractor arms and the second pair of retractor arms are coupled to an expansion assembly for moving the respective pairs of arms between a collapsed position and an expanded position, and each include a substantially irregular outer edge formed substantially along the entire length of each of the individual pairs of arms. This retractor may be placed deep within an incision with the substantially irregular outer edges of the respective pairs of arms being operative engaging substantially the entire length of the edges of the incision, and the tissues beneath the incision, thereby facilitating a high degree of tissue retraction.

BRIEF DESCRIPTION OF THE DRAWINGS

The foregoing and further and more specific objects and advantages of the instant invention will become readily apparent to those skilled in the art from the following detailed description of preferred embodiments thereof taken in conjunction with the drawings in which.

DETAILED DESCRIPTION OF THE PREFERRED EMBODIMENTS

Figure 1:
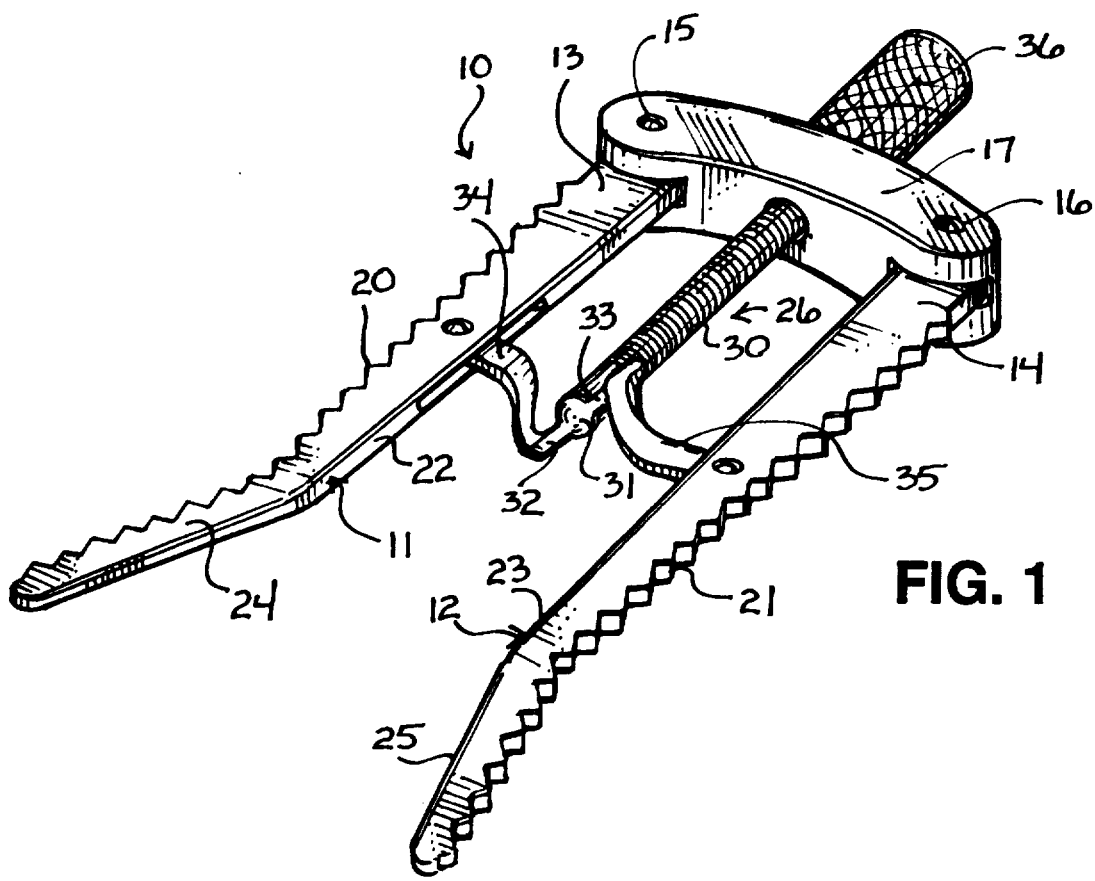
FIG. 1 is a perspective view of a retractor constructed in accordance with the preferred embodiment, the retractor having a pair of retractor arms coupled to an expansion assembly, each retractor arm having an outer engagement edge.

Turning now to the drawings, in which like reference characters indicate corresponding elements throughout the several views, attention is first directed to FIG. 1 which illustrates a first embodiment of the instant invention comprising a retractor being generally designated by the reference character 10. Retractor 10 includes a first retractor portion or arm 11 and a second retractor portion or arm 12 each having an inner end, 13 and 14, respectively, pivotally coupled to the outer ends, 15 and 16, of a base 17 for inwardly and outwardly lateral pivotal movement. First and second retractor arms, 11 and 12, are both generally elongate and each include a substantially irregular outer edge, 20 and 21, an inner edge, 22 and 23, and an outer end, 24 and 25, respectively. Although other irregular formations may be used, substantially irregular outer edges, 20 and 21, are shown configured as serrated for facilitating engagement with tissue as will be discussed shortly. First and second retractor arms, 11 and 12, are disposed parallel to and spaced from one another and are coupled to an expansion assembly 26 operative for moving them between a collapsed position where the first and second retractor arms, 11 and 12, are spaced close to each other, and an expanded position where the first and second retractor arms, 11 and 12, are spaced outwardly from each other.

The expansion assembly 26 includes a substantially elongate threaded element 30 threadably received through a threaded aperture formed through the body of base 17 so as to be positioned intermediate the first and second retractor arms, 11 and 12, and generally within the same plane in which the first and second retractor arms, 11 and 12, reside. Threaded element 30 extends forwardly in the direction towards outer ends, 15 and 16, of retractor arms, 11 and 12, and terminates with an outer end 31 having a pair of opposed elongate armatures, 32 and 33, extending laterally outwardly therefrom. Armatures, 32 and 33, are each coupled to a flexible adjustment element, 34 and 35, respectively, each having an outer end pivotally mounted to first and second retractor arms, 11 and 12, respectively, proximate an intermediate location thereof. Threaded element 30 is coupled to a handle 36 which may be gripped and rotated in a selected direction for pulling the first and second retractor arms, 11 and 12, inwardly together in the collapsed position, or rotated in another direction for pushing the first and second retractor arms, 11 and 12, outwardly apart in the expanded position. It will be readily appreciated by those having ordinary skill that any variety of expansion means may be used in combination with the instant invention for pivotally moving the first and second retractor arms, 11 and 12, inwardly together to the collapsed position, outwardly apart to the expanded position, and any position intermediate the collapsed and expanded position as desired.

Figure 2:
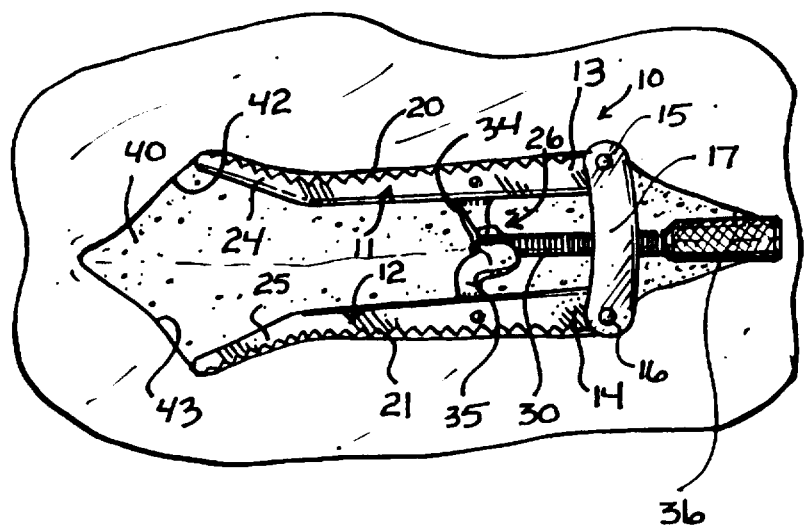
FIG. 2 is a top view of the retractor of FIG. 1 shown as it would appear spreading apart the edges of an incision.

Retractor 10 is operative for holding back the edges of an incision, or otherwise holding back opposing edges of tissue during a surgical procedure as needed by a medical practitioner. In particular, FIG. 2 illustrates an incision 40 formed through portions of a biological organism 41 thereby forming opposing edges, 42 and 43, of tissue. Retractor is shown placed substantially within incision 40 with the respective substantially irregular outer edges, 20 and 21, of first and second retractor arms, 11 and 12, respectively, each engaging one of the opposing edge, 42 and 43, respectively, thereby holding them apart. It will be readily appreciated that opposing edges, 42 and 43, of incision 40 may be selectively spread apart by rotating handle 36 in a selected direction for urging first and second retractor arms, 11 and 12, laterally outwardly thereby pushing opposing edges, 42 and 43, apart.

Each substantially irregular outer edge, 20 and 21, of first and second retractor arms, 11 and 12, constitutes an engagement edge for engaging tissue to be retracted. The irregular nature of each substantially irregular outer edge, 20 and 21, extends substantially along the entire length of the first and second retractor arms, 11 and 12, respectively, from the inner ends, 13 and 14, to outer ends, 24 and 25, respectively. Thus, as can be seen in FIG. 2, substantially irregular outer edges, 20 and 21, facilitate the engagement of substantially the entire length of the opposing edges, 42 and 43, of incision 40, thereby maximizing the degree of tissue retraction along substantially the entire length of the first and second retractor arms, 11 and 12. Accordingly, an extensive degree of tissue retraction is can be accomplished.

With reference back to FIG. 1, first and second retractor arms, 11 and 12, are substantially elongate, with the outer ends, 24 and 25, being provided in outwardly diverging relation respectively. It will be readily understood by those having ordinary skill that other shapes and configurations of retractor arms may be used in combination with the instant invention as needed by a user without departing from the nature and scope of the instant invention as herein specifically described. Additionally, although outer edges, 20 and 21, of first and second retractor arm, 11 and 12, are shown as serrated, they may be provided with other forms of irregularities as selectively desired for facilitating adequate engagement with tissue for facilitating retraction thereof.

Figure 3:
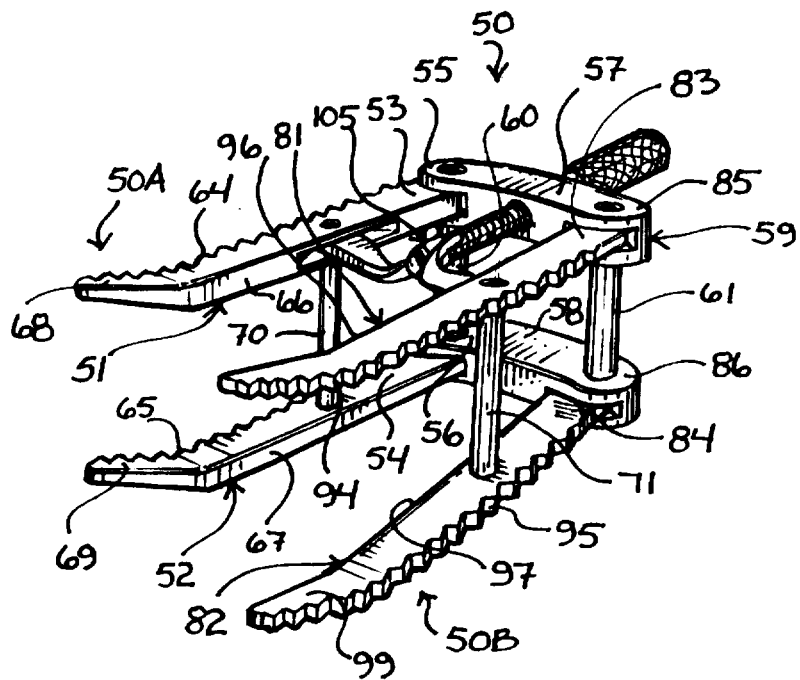
FIG. 3 is a perspective view of an alternate embodiment of a retractor having two pairs of retractor arms.

Attention is now directed to FIG. 3 which illustrates an alternate embodiment of a retractor being generally designated by the reference character 50. Having generally the same operative characteristics as retractor 10, retractor 50 includes a first retractor portion 50A comprised of a first retractor arm 51 and a first lower retractor arm 52 disposed parallel to and spaced from one another. First retractor arm 51 and first lower retractor arm 52 each have an inner end, 53 and 54, pivotally coupled to an outer end, 55 and 56, of upper and lower support elements, 57 and 58, of a base 59 for outward and inward lateral pivotal movement. Upper and lower base elements, 57 and 58, are generally elongate and are substantially rigidly coupled together in spaced apart and substantially parallel relation by means of a pair of spaced apart upright connecting members 60 and 61. First retractor arm 51 and first lower retractor arm 52 are both generally elongate and each include a substantially irregular outer edge, 64 and 65, an inner edge, 66 and 67, an outer end, 68 and 69, respectively, and are substantially rigidly coupled together by means of a first upright column 70 disposed therebetween at a generally intermediate location thereof. Although other irregular formations may be used, substantially irregular outer edges, 64 and 65, extending substantially along the entire length of first retractor arm 51 and first lower retractor arm 52, are shown configured as serrated for facilitating engagement with tissue as fully discussed previously in combination with retractor 10.

Retractor 50 further includes a second retractor portion 50B comprised of a second retractor arm 81 and a second lower retractor arm 82 disposed parallel to and spaced from one another, and further being disposed in parallel and spaced apart relation relative first retractor arm 51 and first lower retractor arm 52, respectively. Second retractor arm 81 and second lower retractor arm 82 each have an inner end, 83 and 84, pivotally coupled to another outer end, 85 and 86, respectively, of upper and lower support elements, 57 and 58, for outward and inward lateral pivotal movement. Second retractor arm 81 and second lower retractor arm 82 are both generally elongate and each further include a substantially irregular outer edge, 94 and 95, an inner edge, 96 and 97, an outer end, 98 and 99, respectively, and are substantially rigidly coupled together by means of a second upright column 71 disposed therebetween at a generally intermediate location thereof. Although other irregular formations may be used, substantially irregular outer edges, 94 and 95 extending substantially along the entire length of second retractor arm 81 and second lower retractor arm 82, are shown configured as serrated for facilitating engagement with tissue as fully discussed previously in combination with retractor 10.

First and second retractor portions, 50A and 50B, are disposed parallel to and spaced from one another with th first and second retractor arms, 51 and 81, of each being coupled to an expansion assembly 105, operative for moving first and second retractor portions, 50A and 50B, between the collapsed position and the expanded configuration discussed previously in combination with retractor 10. Expansion assembly 105 is identical to expansion assembly 26 discussed in combination with retractor 10, and will not be herein again specifically addressed.

Retractor 50 may be inserted deep within an incision, with the first and second retractor portions, 50A and 50B, being operative for retracting a deep and extensive amount of tissue. In particular, the first and second lower retractor arms, 52 and 82, are operative for retracting tissues deep within an incision, and the first and second retractor arms, 51 and 81, are operative for retracting more outlying tissues more towards the surface of the incision. In this manner, the combination of the first and second retractor arms, 51 and 81, and the first and second lower retractor arms, 52 and 82, accommodate an extensive degree of tissue retraction, which may be particularly advantageous when deep access into the body is needed.

Figure 4:
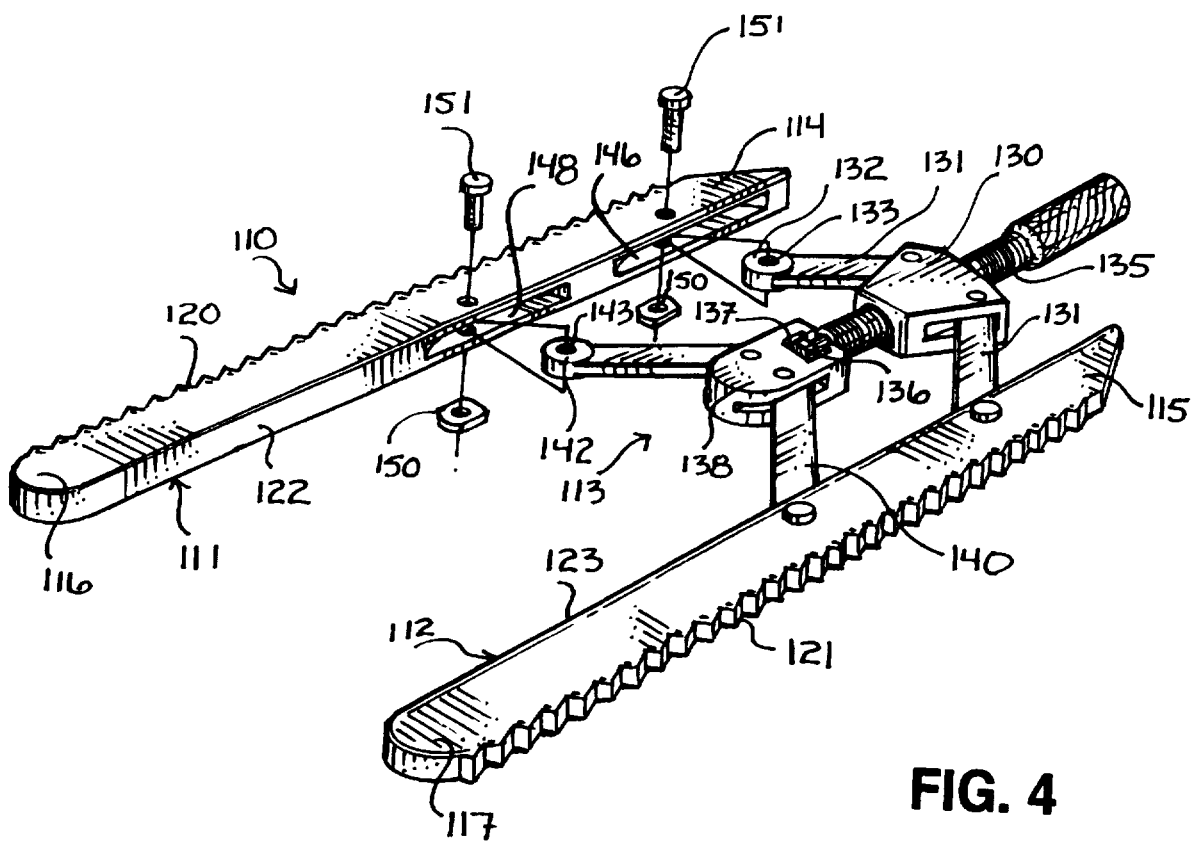
FIG. 4 is a partially exploded perspective view of an alternate embodiment of a retractor having a pair of retractor arms removably coupled to an expansion assembly.

Attention is now directed to FIG. 4 which illustrates yet a further alternate embodiment of a retractor being generally designated by the reference character 110. Retractor 110 includes generally the same structural and functional aspects of retractor 10 discussed previously in combination with FIG. 1 and FIG. 2, with the exception that the individual retractor blades are removably coupled to the expansion assembly and are substantially straight, having a somewhat different configuration as compared to first and second retractor arms, 11 and 12, discussed previously. In particular, like retractor 10, retractor 110 includes a first retractor arm 111 and a second retractor arm 112 coupled together by means of an expansion assembly 113. First and second retractor arms, 111 and 112, are generally elongate and each include an inner end, 114 and 115, an outer end, 116 and 117, a substantially irregular outer edge, 120 and 121, extending along substantially the entire length thereof from inner end, 114 and 115, to outer end, 116 and 117, respectively, and an inner edge, 122 and 123. Although other irregular formations may be used, substantially irregular outer edges, 120 and 121, are shown configured as serrated for facilitating engagement with tissue as discussed with the previously described embodiments. First and second retractor arms, 111 and 112, are disposed parallel to and spaced from one another, with the expansion assembly 113 being operative for moving them between a collapsed position where the first and second retractor arms, 111 and 112, are spaced close to each other in a substantially parallel configuration, and an expanded position where the first and second retractor arms, 111 and 112, are spaced outwardly from each other in a substantially parallel configuration.

Expansion assembly 113, disposed proximate inner ends, 114 and 115, of first and second retractor arms, 111 and 112, respectively, includes a base 130 having a pair of arms 131 pivotally coupled thereto and extending laterally outwardly therefrom in opposing directions, each terminating with an outer end 132 (only one shown) having an aperture 133 (only one shown) extending therethrough. Expansion assembly further includes an elongate threaded element 135 threadably received through a threaded aperture formed through base 130 terminating with a headed end 136 rotatably held within a groove 137 of a forward adjust element 138. Like base 130, forward adjustment element 138 includes pair of arms 140 pivotally coupled thereto and extending laterally outwardly therefrom in opposing directions, each terminating with an outer end 142 (only one shown) having an aperture 143 (only one shown) extending therethrough.

Outer ends, 132 and 142, of the respective pairs of arms, 131 and 140, extending from base 130 and forward adjustment element 138, respectively, are received within grooves, 146 and 148 (shown only in combination with first retractor arm 111), formed through the inner edges, 122 and 123, of first and second retractor arms, 111 and 112, respectively, and are each removably fastened thereto by means of a nut 150 and a bolt 151. Because first and second retractor arms, 111 and 112, are removably coupled to expansion assembly 113, they may be removed as desired, cleaned, and then replaced, or replaced with an alternate pair of retractor arms. It will be understood that retractor arms may be provided in a variety of shapes and sizes specifically suited for meeting the needs of the user. Therefore, it will be readily appreciated that a variety of retractor arms may be constructed and removably coupled to expansion assembly 113 for use thereof as specifically needed.

Various changes and modifications to the embodiment herein chosen for purposes of illustration will readily occur to those skilled in the art. To the extent that such modifications and variations do not depart from the spirit of the invention, they are intended to be included within the scope thereof which is assessed only by a fair interpretation of the following claims.

Having fully described the invention in such clear and concise terms as to enable those skilled in the art to understand and practice the same, the invention claimed is:

1. A retractor for holding back the edges of an incision, said retractor comprising:

a base;

a substantially elongate first retractor arm having an inner end pivotally coupled to said base, an outer end, an inner edge, and a substantially irregular outer engagement edge extending substantially along the entire length of said first retractor arm from said inner end to said outer end thereof;

a substantially elongate second retractor arm having an inner end pivotally mounted to said base, an outer end, an inner edge and a substantially irregular outer engagement edge extending along substantially the entire length of said second retractor arm from said inner end to said outer end thereof, said first retractor arm being disposed parallel to and spaced from said second retractor arm;

an expansion assembly coupled to said first retractor arm and said second retractor arm for moving said first retractor arm and said second retractor arm between a contracted and an expanded position, said substantially irregular outer engagement edge of said first retractor arm and said substantially irregular engagement edge of said second retractor arm for engaging the edges of the incision.

2. The retractor of claim 1, wherein said substantially irregular outer engagement edge of said first retractor arm includes a plurality of serrations extending along substantially the entire length thereof from said inner end to said outer end.

3. The retractor of claim 1, wherein said substantially irregular outer engagement edge of said second retractor arm includes a plurality of serrations extending along substantially the entire length thereof from said inner end to said outer end.

4. The retractor of claim 1, wherein said first retractor arm and said second retractor arm are removably coupled to said expansion assembly.

5. A retractor for holding back the edges of an incision, said retractor comprising:

a base;

a substantially elongate first retractor arm having an inner end pivotally coupled to said base, an outer end, an inner edge, and a substantially irregular outer engagement edge extending substantially along the entire length of said first retractor arm from said inner end to said outer end thereof;

a substantially elongate first lower retractor arm having an inner end pivotally coupled to said base, an outer end, an inner edge, and a substantially irregular outer engagement edge extending along substantially the entire length of said first lower retractor arm from said inner end to said outer end thereof, said first lower retractor arm being substantially rigidly coupled to, and disposed substantially parallel to and spaced from, said first retractor arm;

a substantially elongate second retractor arm having an inner end pivotally mounted to said base, an outer end, an inner edge and a substantially irregular outer engagement edge extending along substantially the entire length of said second retractor arm from said inner end to said outer end thereof, said second retractor arm being disposed parallel to and spaced from said first retractor arm;

a substantially elongate second lower retractor arm having an inner end pivotally coupled to said base, an outer end, an inner edge, and a substantially irregular outer engagement edge extending along substantially the entire length of said second lower retractor arm from said inner end to said outer end thereof, said second lower retractor arm being substantially rigidly coupled to, and disposed substantially parallel to and spaced from, said second retractor arm; and an expansion assembly coupled to said first retractor arm and said second retractor arm for moving said first retractor arm and said first lower retractor arm, and said second retractor arm and said second lower retractor arm, respectively, between a contracted and an expanded position, each said substantially irregular outer engagement edge of said first retractor arm, said first lower retractor arm, said second retractor arm and said second lower retractor arm for engaging substantially the entire length of the edges of the incision.

6. The retractor of claim 5, wherein said substantially irregular outer engagement edge of said first retractor arm includes a plurality of serrations extending along substantially the entire length thereof from said inner end to said outer end.

7. The retractor of claim 5, wherein said substantially irregular outer engagement edge of said second retractor arm includes a plurality of serrations extending along substantially the entire length thereof from said inner end to said outer end.

8. The retractor of claim 5, wherein said substantially irregular outer engagement edge of said first lower retractor arm includes a plurality of serrations extending along substantially the entire length thereof from said inner end to said outer end.

9. The retractor of claim 5, wherein said substantially irregular outer engagement edge of said second lower retractor arm includes a plurality of serrations extending along substantially the entire length thereof from said inner end to said outer end.

* * * * *